(12) United States Patent
Zhang

(10) Patent No.: US 10,669,308 B2
(45) Date of Patent: Jun. 2, 2020

(54) METHOD CAPABLE OF BEING USED FOR PROTEIN RENATURATION INDEPENDENTLY OR BEING USED AS PRECEDING OPERATIONS OF PROTEIN RENATURATION

(71) Applicant: Peng Zhang, Jinan (CN)

(72) Inventor: Peng Zhang, Jinan (CN)

( * ) Notice: Subject to any disclaimer, the term of this patent is extended or adjusted under 35 U.S.C. 154(b) by 23 days.

(21) Appl. No.: 15/840,024

(22) Filed: Dec. 13, 2017

(65) Prior Publication Data

US 2018/0099992 A1 Apr. 12, 2018

Related U.S. Application Data

(63) Continuation of application No. PCT/CN2015/081480, filed on Jun. 15, 2015.

(51) Int. Cl.
*C07K 1/30* (2006.01)
*C07K 1/113* (2006.01)

(52) U.S. Cl.
CPC ............ *C07K 1/30* (2013.01); *C07K 1/1136* (2013.01)

(58) Field of Classification Search
None
See application file for complete search history.

(56) References Cited

U.S. PATENT DOCUMENTS

| | | | |
|---|---|---|---|
| 5,912,327 A * | 6/1999 | Li | C07K 1/113 435/252.3 |
| 2010/0121032 A1 * | 5/2010 | Cox | C07K 14/57 530/351 |

FOREIGN PATENT DOCUMENTS

| | | |
|---|---|---|
| CN | 1786017 | 6/2006 |
| CN | 101565448 | 10/2009 |
| WO | 0155174 | 8/2001 |

OTHER PUBLICATIONS

Gujjari P, et al. "Effect of cryopreservation protocols on the phenotypic stability of yeast", Cryo Letters May-Jun.;31(3): 261-7 (2010) (Year: 2010) (Abstract Only).*
WIPO, English translation of the ISR/WO for PCT/CN2015/081480, Jan. 29, 2016.
Emily J. Guinn et al.; "Probing the Protein-Folding Mechanism Using Denaturant and Temperature Effects on Rate Constants", PNAS, vol. 110, No. 42, Sep. 16, 2003, pp. 16784-16789.
Bohr et al., "Microwave-enhanced folding and denaturation of globular proteins," Physical Review E, The American Physical Society, Apr. 2000, vol. 61, No. 4, pp. 4310-4314.
Li et al., "Research Progress of Inclusion Body Refolding Technology," Chinese medical biotechnology, Aug. 2012, vol. 7, No. 4, 12 pages.
Ohshima et al., "Influence of pulsed electric field on various enzyme activities," Journal of Electrostatics, 2007, vol. 55, pp. 156-161.
St. John et al., "High pressure fosters protein refolding from aggregates at high concentrations," PNAS, Nov. 1999, vol. 96, No. 23, pp. 13029-13033.
SIPO, First Office Action for CN Application No. 201510450732.5, dated Feb. 3, 2020.

* cited by examiner

*Primary Examiner* — Anand U Desai
(74) *Attorney, Agent, or Firm* — Hodgson Russ LLP

(57) ABSTRACT

Provided is a method of treating a protein to be renatured, including: (1) mixing the protein to be renatured with a denaturing solution containing a denaturing reagent; (2) incubating a resulting mixture at such a low temperature that the denaturing agent is gradually precipitated from the denaturing solution, resulting in a decreasing concentration gradient of the denaturing agent and an increasing concentration of a renatured protein or its precursor in the denaturing solution with a decreasing volume; and (3) obtaining at least one of the renatured protein and its precursor.

16 Claims, 2 Drawing Sheets

US 10,669,308 B2

METHOD CAPABLE OF BEING USED FOR PROTEIN RENATURATION INDEPENDENTLY OR BEING USED AS PRECEDING OPERATIONS OF PROTEIN RENATURATION

CROSS-REFERENCE TO RELATED APPLICATIONS

The present application is a continuation application of PCT Application No. PCT/CN2015/081480 filed on Jun. 15, 2015, the entire content of which is incorporated herein by reference.

FIELD

The present disclosure relates to the field of basic biotechnology, in particular to a method of treating a protein to be renatured.

BACKGROUND

The most common methods for renaturing a protein, such as an aggregate or an inclusion body, mainly involve dilution, chromatography and dialysis. Such three methods have a same principle for refolding a protein, that is, since the protein in an active site is of the lowest energy level of a protein molecule, an internal structure of a peptide chain in a protein to be renatured is rearranged spontaneously at a decreasing concentration of a denaturing agent in a denaturing solution, thereby minimizing the energy level of the protein molecule in the protein gradually, thus the activity of the protein is recovered. However, it is inevitable to avoid the peptide chain from aggregating because of a thermal motion of the protein molecule, which will lead to a failure of protein renaturation. The chromatography method has many disadvantages, such as high requirement, expensive column stuffs, low throughput, strict conditions, complex optimization of the column stuffs, and so on. Although being capable of obtaining a product in a high concentration, the dialysis method is easily to cause precipitation. The dilution method, mostly used in the current research application and production, and being substantially to renature a protein to be renatured by diluting a renaturation solution gradually, is mostly optimized by altering components of the renaturation solution and proportions thereof, the conditions for dilution and so on, so as to improve the renaturation efficiency of the protein, compared to a 10% renaturation yield obtained in the present dilution method. Nevertheless, it is impossible to avoid the sample from being diluted excessively.

Therefore, there is still a need to further improve the existing method for renaturing a protein.

SUMMARY

Embodiments of the present disclosure seek to solve at least one of the problems existing in the related art to at least some extent. An object of the present disclosure is to provide a method of treating a protein to be renatured based on increasing precipitation of a denaturing agent from a denaturing solution by means of a programmed cooling process at a low temperature, which prepares at least one of the renatured protein and its precursor. As such, with the present method of treating the protein to be renatured, on one hand, the renatured protein is obtained effectively and directly, so that the present method can be used as an independent method for renaturing a protein to be renatured; on the other hand, the precursor obtained is in a more correctly refolded structure or state suitable for being further renatured to become the renatured protein, thus the present method can also be used as a preceding operation for the method for renaturing a protein to be renatured. In addition, during the present method, the denaturing agent precipitated and the denaturing solution containing unrenatured protein are allowed to be recycled, and the decreased volume of the denaturing solution benefits for follow-up steps, thereby decreasing preparation cost of the protein renaturation to a great extent, and protecting environment from pollution caused by the denaturing agent.

In a first aspect, the present disclosure provides in embodiments a method of treating a protein to be renatured, including steps as follows:

(1) mixing the protein to be renatured with a denaturing solution containing a denaturing reagent;

(2) incubating a resulting mixture at such a low temperature that the denaturing agent is gradually precipitated from the denaturing solution, resulting in a decreasing concentration gradient of the denaturing agent and an increasing concentration of a renatured protein or its precursor in the denaturing solution with a decreasing volume; and (3) obtaining at least one of the renatured protein and its precursor.

In some embodiments of the present disclosure, the at least one of the renatured protein and its precursor is present in at least one form of a solution and a frozen body.

In some embodiments of the present disclosure, the present method further includes a step (4) of subjecting the at least one of the renatured protein and its precursor obtained in the step (3) to an additional renaturing process, such that the precursor is further renatured to become the renatured protein.

In some embodiments of the present disclosure, the renaturing process includes at least one of a dilution method, a dialysis method, a chromatography method, shear stress-mediated refolding and reverse micelle extraction.

In some embodiments of the present disclosure, in step (2), the resulting mixture is incubated under at least one of an electric field, a magnetic field, a high pressure and a sound wave.

In some embodiments of the present disclosure, the denaturing agent is a chemical agent adapted for opening a secondary bond effectively so as to keep a peptide chain in a free extended condition.

In some embodiments of the present disclosure, the denaturing agent is selected from at least one of urea and guanidine hydrochloride.

In some embodiments of the present disclosure, the denaturing agent is of an initial concentration greater than 4 mol/L.

In some embodiments of the present disclosure, the denaturing solution further includes a reducing agent and a cryoprotective agent.

In some embodiments of the present disclosure, the reducing agent is a material capable of destroying a disulfide bond so as to produce a reduced thiol.

In some embodiments of the present disclosure, the reducing agent is selected from one or more of dimercaptoethanol, dithiothreitol, tris-(2-carboxyethyl)phosphine, reduced glutathione, hydrogen sulfide, ascorbic acid and sodium thiosulfate.

In some embodiments of the present disclosure, the cryoprotective agent is selected from one or more of a skim milk, a gelatin, a protein, a protein hydrolysate, a polypeptide, a yeast, a broth, a dextrin, methylcellulose, serum, peptone, sodium thiosulfate, calcium lactate, sodium glutamate, sodium chloride, potassium chloride, sodium sulfate, ammonium acetate, ammonium chloride, sucrose, lactose, fucose, maltose, glucose, raffinose, fructose, hexose, sorbitol, ethanol, ethylene glycol, glycerol, mannitol, inositol, xylitol, citric acid, phosphoric acid, tartaric acid, amino acid, ethylenediaminetetraacetic acid, sodium hydroxide, sodium bicarbonate, dextran, polyethylene glycol and PVP.

In some embodiments of the present disclosure, the denaturing solution is of a pH value of 4.0 to 10.0.

In some embodiments of the present disclosure, the low temperature in the step (2) is below 4° C.

In some embodiments of the present disclosure, the protein to be renatured in the denaturing solution is of an initial concentration of 0.001 μg/ml to 30 mg/ml.

In some embodiments of the present disclosure, at least a part of the protein to be renatured is in a structural form of an inclusion body.

In some embodiments of the present disclosure, the step (2) is conducted in a container provided with at least one snubber partition disposed along a horizontal or vertical direction.

In some embodiments of the present disclosure, each snubber partition is of a cross section consisting of a plurality of equilateral polygons.

In some embodiments of the present disclosure, the cross section is in a honeycomb shape consisting of a plurality of hexagons with a side length of 0.5 cm to 4.0 cm.

In some embodiments of the present disclosure, at least two snubber partitions are disposed along the horizontal or vertical direction and parallel to each other, with the equilateral polygons in different snubber partitions in a same shape but in same or different side lengths.

Additional aspects of the disclosure and advantages thereof will be set forth and will become apparent partly in the following description, or may be understood by practice of the disclosure.

DESCRIPTION OF DRAWINGS

The foregoing and/or additional aspects of the present invention and advantages thereof will become apparent and easily understood from the following description of the embodiments combined with the following figures, in which.

DETAILED DESCRIPTION

Figure 1:
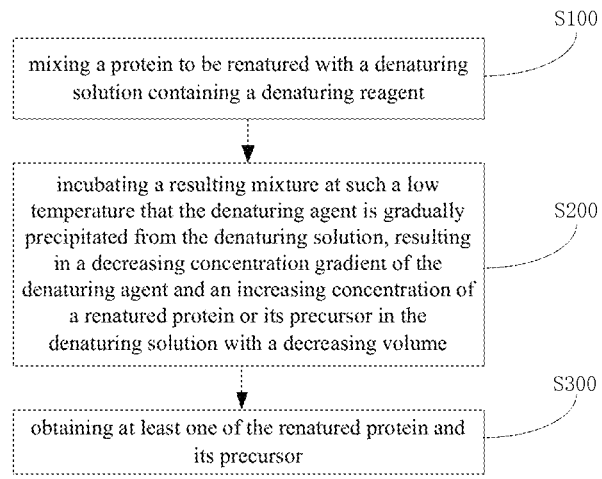
FIG. 1 is a flow chart showing a method of treating a protein to be renatured according to some embodiments of the present disclosure.
Figure 2:
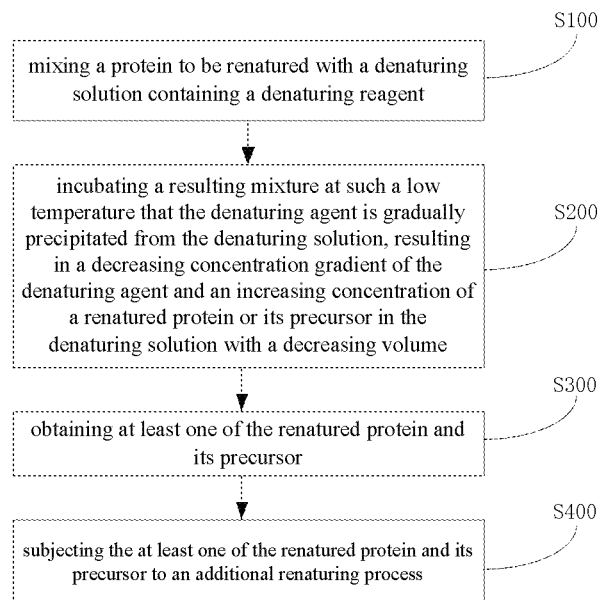
FIG. 2 is a flow chart showing a method of treating a protein to be renatured according to other embodiments of the present disclosure.

Embodiments of the present disclosure are described in detail below, and exemplary embodiments are shown in the drawings. Throughout the description, like or similar reference numerals refer to like or similar elements or elements having the same or similar functions. The embodiments described below with reference to the drawings are exemplary, and they are intended to be illustrative of the disclosure and are not to be construed to limit the disclosure.

In an aspect of embodiments of the present disclosure, provided is a method of treating a protein to be renatured, including:

(1) mixing the protein to be renatured with a denaturing solution containing a denaturing reagent;

(2) incubating a resulting mixture at such a low temperature that the denaturing agent is gradually precipitated from the denaturing solution, resulting in a decreasing concentration gradient of the denaturing agent and an increasing concentration of a renatured protein or its precursor in the denaturing solution with a decreasing volume; and (3) obtaining at least one of the renatured protein and its precursor.

According to some embodiments of the present method, the denaturing agent is gradually precipitated from the denaturing solution by means of a programmed cooling process at a low temperature, resulting in a decreasing concentration gradient of the denaturing agent, such that the denaturation ability is decreased and the activity of the protein to be renatured is recovered gradually, thereby obtaining at least one of the renatured protein and its precursor. Compared to the existing dilution method for renaturing a protein, the present method has many advantages, for example, almost no tail solution is produced; the thermal motion of the protein molecule is suppressed at a low temperature, thereby decreasing uncorrected refolding of the protein owing to decrease of collision between peptide chains (in which such uncorrected refolding of the protein leads to a chain reaction and lots of precipitations which may result in a failure of protein renaturation and even severe damage to a device used), thereby improving the renaturation efficiency of the protein; the initial concentration of the denaturing solution is not limited strictly and the denaturing agent precipitated is allowed to be recycled easily, thereby reducing preparation cost of the renatured protein; and a concentration of the renatured protein is increased dramatically as the volume of the denaturing solution is decreased due to precipitation of the denaturing agent from the denaturing solution.

Referring to FIG. 1, based on the embodiments of the present disclosure, the method of treating a protein to be renatured will be described in detail as follows S100 to S300.

S100: mixing the protein to be renatured with a denaturing solution containing a denaturing reagent.

In some embodiments of the present disclosure, the protein to be renatured is mixed with a denaturing solution. In a specific embodiment, the denaturing solution may contain a denaturing agent.

In some embodiments of the present disclosure, the denaturing agent is a chemical agent adapted for opening a secondary bond effectively so as to keep a peptide chain in a free extended condition, for example, the denaturing agent is selected from at least one of urea and guanidine hydrochloride, thereby improving the renaturation efficiency of the protein significantly.

In some embodiments of the present disclosure, the initial concentration of the denaturing solution is not limited strictly, so as to decrease the cost of the denaturing agent significantly.

In a specific embodiment, the urea and the guanidine hydrochloride each are of an initial concentration greater than 4 mol/L, thereby further improving the renaturation efficiency of the protein.

In some embodiments of the present disclosure, the denaturing solution further contains a reducing agent and a cryoprotective agent.

Specifically, the urea and the guanidine hydrochloride used as the denaturing agent makes incorrectly folded peptide chains unstable to a great extent, thereby facilitating the peptide chains to unfold, while the reducing agent adapted to open a disulfide bond makes incorrectly bound disulfide bonds unstable and facilitates the peptide chains to refold in a correct way, thus significantly improving the renaturation efficiency of the protein. It should be noted that the concentration of the reducing agent may be increased or decreased depending on the number of the disulfide bonds in a protein during renaturation.

In a specific embodiment of the present disclosure, the reducing agent may be a material capable of destroying a disulfide bond so as to produce a reduced thiol.

In a specific embodiment of the present disclosure, the reducing agent may be selected from one or more of dimercaptoethanol, dithiothreitol, tris-(2-carboxyethyl) phosphine, reduced glutathione, ascorbic acid, hydrogen sulfide and sodium thiosulfate, thereby opening mismatched disulfide bonds effectively by a reduction reaction, promoting dissolution of the inclusion body and allowing exchange of oxidation-reduction electron pairs, thus facilitating the incorrectly folded peptide chains to refold in a correct way.

In a specific embodiment of the present disclosure, the cryoprotective agent may be selected from one or more of a skim milk, a gelatin, a protein, a protein hydrolysate, a polypeptide, a yeast, a broth, a dextrin, methylcellulose, serum, peptone, sodium thiosulfate, calcium lactate, sodium glutamate, sodium chloride, potassium chloride, sodium sulfate, ammonium acetate, ammonium chloride, sucrose, lactose, fucose, maltose, glucose, raffinose, fructose, hexose, sorbitol, ethanol, ethylene glycol, glycerol, mannitol, inositol, xylitol, citric acid, phosphoric acid, tartaric acid, amino acid, ethylenediaminetetraacetic acid, sodium hydroxide, sodium bicarbonate, dextran, polyethylene glycol and PVP, thus maintaining the activity of the protein at a low temperature.

The inventor found that such a cryoprotective agent is capable of decreasing an ice point of the reaction solution, and has excellent effects of maintaining the solution in a liquid form, thereby further contributing to retaining the activity of the protein at a low temperature. However, the cryoprotective agent is also capable of facilitating precipitation of the denaturing agent. The inventor also found that the cryoprotective agent, consisting of 25% (w/v)sucrose solution and 10 volume % glycerinum, is significantly superior to other cryoprotective agents in maintaining the activity of the protein and improving the viscosity of the solution at a low temperature, thereby decreasing the collisions between the protein molecules and facilitating the peptide chains to refold correctly, thus improving the renaturation efficiency of the protein.

In a special embodiment of the present disclosure, the denaturing solution may be of a pH value of 4.0 to 10.0, preferably 6.5 to 8.5, more preferably 7.0 to 8.0, thereby further improving the renaturation efficiency of the protein.

In a specific embodiment of the present disclosure, the protein to be renatured in the denaturing solution may be of an initial concentration of 0.001 μg/ml to 30 mg/ml, preferably 0.05 μg/ml, 0.1 μg/ml, 1 μg/ml, 5 μg/ml, 10 μg/ml, 20 μg/ml, 30 μg/ml, 50 μg/ml, 70 μg/ml, 100 μg/ml, 200 μg/ml, 300 μg/ml, 500 μg/ml, 700 μg/ml, 1 mg/ml, 5 mg/ml, 10 mg/ml, 15 mg/ml, 17 mg/ml, 20 mg/ml, 25 mg/ml or 30 mg/ml, more preferably 100 μg/ml, 500 μg/ml or 5 mg/ml, most preferably 0.1 mg/ml, thereby further improving the renaturation efficiency of the protein.

In a specific embodiment of the present disclosure, at least a part of the protein to be renatured is in a structural form of an inclusion body. For example, the protein to be renatured may be an inactive epidermal growth factor (EGF), or may be an EGF inclusion body expressed by *Escherichia coli*. In particular, the EGF inclusion body may be obtained by the following steps that genetically engineered *Escherichia coli* BL21 (pet30b-EGF) having been cultured in a culture dish is incubated in 1 L lysogeny broth (LB) culture medium, and 300 μM IPTG is added when an optical density (OD) value of the culture medium reaches 0.8; the mixture is induced at 16° C. for overnight, after which the bacteria solution obtained is centrifuged, washed three times with the Tris buffer (Tris-HCl 20 mmol/L, pH 7.5), and subjected to ultrasonication and centrifugation; the precipitation obtained is washed five times with the Triton 100 buffer (Tris-HCl 20 mmol/L, pH7.5, EDTA 10 mmol/L, NaCl 0.5 mol/L, Triton X-100, 1%) and then ethanol, followed by heating to dryness.

S200: allowing the denaturing agent to be gradually precipitated from the denaturing solution at a low temperature.

In some embodiments of the present disclosure, the denaturing agent is allowed to be gradually precipitated from the denaturing solution, resulting in a decreasing concentration gradient of the denaturing agent, such that the denaturation ability of the denaturing agent is decreased and the activity of the protein to be renatured is recovered gradually, thereby obtaining the renatured protein or its precursor. Compared to the existing dilution method for renaturing a protein, the present method has many advantages, for example, almost no tail solution is produced; the initial concentration of the denaturing solution is not limited strictly and the denaturing agent precipitated is allowed to be recycled; and the concentration of the renatured protein is increased greatly as the denaturing solution is of a decreased volume due to precipitation of the denaturing agent, thus, the renaturation efficiency of the protein is improved and the preparation cost for renaturation is further shortened.

In some embodiments of the present disclosure, the at least one of the renatured protein and its precursor is present in at least one form of a solution and a frozen body, thereby facilitating for follow-up steps. According to embodiments of the present disclosure, the present method allows the concentration of the denaturing agent to decrease smoothly mainly depending on the programmed change of the temperature. In a specific embodiment, the low temperature is below 4° C. In another specific embodiment, the container containing the protein to be renatured and the denaturing solution is placed at a low temperature below zero and subjected to a programmed cooling process; the denaturing agent (such as urea) is precipitated gradually as crystals, with a decreasing concentration gradient of the denaturing agent formed in the denaturing solution. The crystals of the denaturing agent are taken out when achieving to a substantial amount, and the remaining mixture is continually cooled till an ice block appears in the upper layer and the crystals newly-precipitated in the lower layer. The ice block is then taken out when a clear boundary is present between the upper layer and the lower layer, and then transferred into a centrifuge tube and frozen at −20° C. for store.

In the prior art, during renaturing a protein by all the existing methods, the reaction solution is under flow because of stirring, passing through a column and so on, such that the thermal motion of the protein molecule and the collisions between peptide chains are increased, thereby causing aggregation or even precipitation of the peptide chains to some extent. The inventor also found that, when the present method is conducted in a container provided with at least one snubber partition disposed along a horizontal or vertical direction which is capable of controlling convection of the reaction solution, the protein to be renatured in the solution can be ensured to be renatured in a stationary environment, and the low-temperature may further benefit for the stationary environment owing to the decreased thermal motion of the protein molecule and the decreased collisions between the peptide chains, thus facilitating the disulfide bonds or secondary bonds mismatched in the primary structure of the protein to be renatured in a correct way.

In some embodiments of the present disclosure, the present method may be conducted in a container provided with at least one snubber partition, with the partition arranged in any forms that is capable of controlling the convection of the reaction solution, such as vertically, horizontally, vertically and horizontally, or so on, preferably along a vertical direction, and each snubber partition being of a cross section consisting of a plurality of equilateral polygons, by which the interior space of the container is divided into several parts, thereby guaranteeing the solution being renatured in a stationary environment, thus improving the renaturation efficiency of the protein.

In some embodiments of the present disclosure, the snubber partition is made of metal materials, such as Aluminum, Iron and so on, which is coated with plastics in the surface, so as to facilities heat loss.

Figure 3:
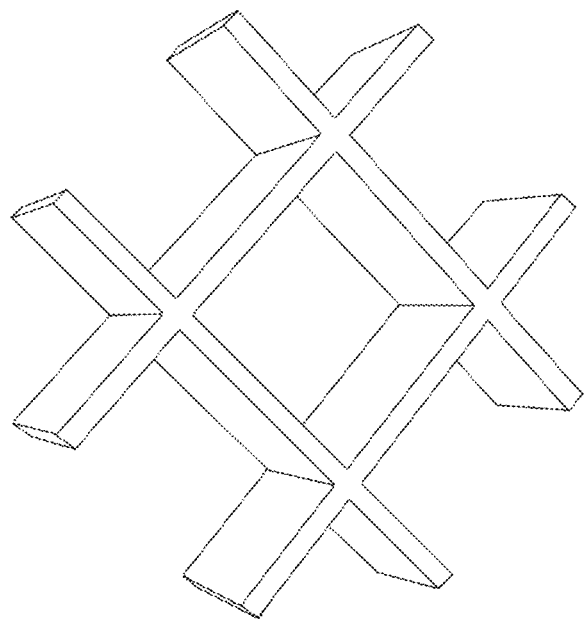
FIG. 3 is a schematic graph showing a snubber partition according to an embodiment of the present disclosure.
Figure 4:
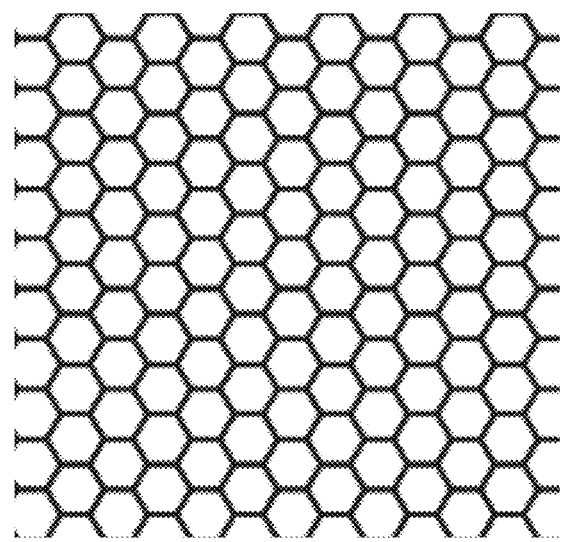
FIG. 4 is a schematic graph showing a snubber partition in a honeycomb shape consisting of a plurality of hexagons according to an embodiment of the present disclosure.

In a specific embodiment of the present disclosure, the snubber partition is disposed along a vertical and horizontal direction, with a square cross section, as shown in FIG. 3, thereby guaranteeing the solution being renatured in a stationary environment, thus improving the renaturation efficiency of the protein. In a specific embodiment of the present disclosure, the snubber partition is in a honeycomb shape consisting of a plurality of hexagons, as shown in FIG. 4, thereby guaranteeing the solution being renatured in a stationary environment, thus improving the renaturation efficiency of the protein.

In some embodiments of the present disclosure, the cross section is in a honeycomb shape consisting of a plurality of hexagons with a side length of 0.5 cm to 4.0 cm, thereby facilitating to control the convection of the reaction solution, and guaranteeing the solution being renatured in a stationary environment.

In some embodiments of the present disclosure, at least two snubber partitions are disposed along the horizontal or vertical direction, preferably vertical direction, and parallel to each other, with the equilateral polygons in different snubber partitions in a same shape but in same or different side lengths, thereby guaranteeing the solution being renatured in a stationary environment, thus improving the renaturation efficiency of the protein. The inventor also found that, when the solution containing the protein to be renatured is incubated in a stationary environment under at least one of an electric field, a magnetic field, a high pressure and a sound wave, the peptide chains of the protein seem to be vibrated slightly which may further cause them to collapse, thereby benefiting them to form a secondary structure or a tertiary structure, thus improving the renaturation efficiency of the protein. In addition, when the electric field is applied, the solution may create an induced electric field instantaneous which is opposite in direction and equal in magnitude to the electric field applied, because of lots solutes presented in the solution, such as a denaturing agent, peptide chains and so on, thereby facilitating the peptide chains to be arranged more regularly owing to the different charges at two ends of the peptide chains, and further suppressing the Brownian motion of the protein molecules, preventing mismatch of the peptide chains and improving the renaturation efficiency.

In a special embodiment of the present disclosure, the solution containing a protein to be renatured is incubated under at least one of an electric field, a magnetic field, a high pressure, and a sound wave during renaturation, so that the peptide chains of the protein in the solution will be vibrated and further be collapsed, thereby benefiting them to form a secondary structure or a tertiary structure, thus improving the renaturation efficiency of the protein.

Meantime, the solution may be subjected to centrifugation so as to precipitate tiny crystals formed which are not precipitated easily under a low temperature, because of increased solution viscosity, thereby further improving the renaturation efficiency of the protein.

S300: obtaining at least one of the renatured protein and its precursor.

In some embodiments of the present disclosure, at least one of the renatured protein and its precursor is obtained. In this step, the ice block containing the renatured protein and/or its precursor and formed in the upper layer of the denaturing solution may be taken out directly, or the denaturing solution containing the renatured protein and/or its precursor unfrozen into the ice block may be taken out with a straw or divided directly into parts with the partitions followed by subsequent treatments.

In some embodiments of the present method, after steps S100 to S300, the renatured protein without its precursor can be obtained effectively and directly, thus the present method can be used as an independent method for renaturing a protein to be renatured.

In other embodiments of the present method, after steps S100 to S300, the precursor of renatured protein is at least obtained, which is in a more correctly refolded structure or state suitable for being further renatured to become the renatured protein, thus the present method can also be used as a preceding operation for the method for renaturing a protein to be renatured.

In some embodiments of the present disclosure, the present method further includes a step (4) of subjecting the at least one of the renatured protein and its precursor obtained in the step (3) to an additional renaturing process, thereby facilitating the renaturation of the protein precursor.

In some embodiments of the present disclosure, the renaturing process includes at least one of a dilution method, a dialysis method, a chromatography method, shear stress-mediated refolding and reverse micelle extraction.

In some embodiments of the present disclosure, the denaturing agent is gradually precipitated from the denaturing solution by means of the programmed cooling process at the low temperature, resulting in the decreasing concentration gradient of the denaturing agent in the denaturing solution, such that the denaturation ability of the denaturing agent is decreased and the activity of the protein to be renatured is recovered gradually, thereby obtaining at least one of the renatured protein and its precursor. Compared to the existing dilution method for renaturing a protein, the present method has many advantages, for example, almost no tail solution is produced; the initial concentration of the denaturing solution is not limited strictly and the denaturing agent precipitated is allowed to be recycled; and the concentration of the renatured protein is increased dramatically as the volume of the denaturing solution is decreased due to precipitation of the denaturing agent from the denaturing solution, thus, the renaturation efficiency of the protein is improved and the preparation cost for renaturing the protein is lowered.

The embodiments of the present disclosure will be described with reference to the following examples. It will be understood by those skilled in the art that the following examples are intended to be illustrative and should not be construed as limiting of the scope of the disclosure in any ways.

EXAMPLE

Example 1

Firstly, 8 mol/L aqueous urea (250 mL) was mixed with 50 μL dimercaptoethanol, thus obtaining a denaturing solution; then 20 mg crushed EGF inclusion body was mixed with 200 mL of the denaturing solution obtained, thus obtaining a first inclusion body solution in a concentration of 0.1 mg/ml; to the first inclusion body solution obtained, 50 g of 25 wt % sucrose and 20 mL of 10 wt % glycerinum were added, thus obtaining a second inclusion body solution which was adjusted to be of a pH value of 7 to 8 with a sodium carbonate solution; the resulting mixture was subjected to a programmed cooling process at −20° C., and urea crystals were taken out when formed in substantial amounts; the remaining mixture was continually cooled, with an ice block appeared in the upper layer and another urea crystals precipitated in the lower layer; the ice block was taken out when a clear demarcation boundary was appeared between the upper layer and the lower layer, then transferred into a centrifuge tube and frozen at −20° C., thus obtaining a mixture containing a renatured protein and its precursor; finally, three random aliquots of the sample mixture were detected by the epidermal growth factor (EGF) ELISA kit (Boster Biological Technology co. LTD, EK0326) for their activities, according to the manufacturer's instructions, with yellow color indicating the presence of activated proteins; and another three random aliquots of the sample solution were detected by the WD-2102A automatic microplate reader (Beijing, Liu Yi) for their absorbance, with the detected results shown in Table 1 as follows.

TABLE 1

Absorbance of Each Sample

| NO. | Absorbance |
|---|---|
| Blank Control | 0.001 |
| Sample 1 | 0.135 |
| Sample 2 | 0.152 |
| Sample 3 | 0.139 |

Example 2

Firstly, 8 mol/L aqueous urea (2000 mL) was mixed with 0.2 mL dimercaptoethanol, thus obtaining a denaturing solution; then 140 mg crushed EGF inclusion body was mixed with 1400 mL of the denaturing solution obtained, thus obtaining a first inclusion body solution in a concentration of 0.1 mg/ml; to the first inclusion body solution obtained, 100 mL glycerinum was added as a cryoprotective agent, and used to adjust the ice point of the solution, thus obtaining a second inclusion body solution which was further adjusted to be of a pH value of 7.1 with a sodium carbonate solution; the container used for renaturing the EGF inclusion body was coated with several towels for keeping cool; the resulting mixture was subjected to a programmed cooling process at −20° C., and urea crystals were taken out when formed in substantial amounts; an ice block formed in the upper layer was taken out and then subjected to thaw, thus obtaining a mixture containing a renatured protein and its precursor. Finally, three random aliquots of the sample mixture were detected by the epidermal growth factor (EGF) ELISA kit (Boster Biological Technology co. LTD, EK0326) for their activities, according to the manufacturer's instructions, with yellow color indicating the presence of activated proteins; and another three random aliquots of the sample mixture were detected by the WD-2102A automatic microplate reader (Beijing, Liu Yi) for their absorbance, with the detected results shown in Table 2 as follows.

TABLE 2

Absorbance of Each Sample

| No. | Absorbance |
|---|---|
| Blank Control | 0.001 |
| Sample 1 | 0.089 |
| Sample 2 | 0.100 |
| Sample 3 | 0.104 |

Example 3

Firstly, 8 mol/L aqueous urea (2000 mL) was mixed with 0.2 mL dimercaptoethanol, thus obtaining a denaturing solution; then 140 mg crushed EGF inclusion body was mixed with 1400 mL of the denaturing solution obtained, thus obtaining a first inclusion body solution in a concentration of 0.1 mg/ml; to the first inclusion body solution obtained, 100 mL glycerinum was added as a cryoprotective agent, and used to adjust the ice point of the solution, thus obtaining a second inclusion body solution which was further adjusted to be of a pH value of 7.1 with a sodium carbonate solution; the container used for renaturing the EGF inclusion body was coated with several towels for keeping cool; the resulting mixture was subjected to a programmed cooling process at −16° C. overnight; in the upper layer of the mixture, the supernatant without a precipitated urea crystal was transferred into a centrifuge tube, and then subjected to other renaturation methods, such as dilution, chromatography, dialysis or their combination, thus obtaining a first mixture containing a renatured protein and its precursor; the first mixture obtained was diluted by 5 times with the epidermal growth factor (EGF) ELISA kit (Boster Biological Technology co. LTD, EK0326), thus obtaining a second mixture; finally, three random aliquots of each of the first mixture and the second mixture were detected respectively by the EGF ELISA kit for their activities, according to the manufacturer's instructions, with yellow color indicating the presence of activated proteins; and another three random aliquots of each of them were detected respectively by the WD-2102A automatic microplate reader (Beijing, Liu Yi) for their absorbance, with the detected results shown in Table 3 as follows.

TABLE 3

Absorbance of Each Sample

| No. | Absorbance | |
| --- | --- | --- |
| | Before dilution | After dilution by 5 times |
| Blank Control | 0.002 | 0.000 |
| Sample 1 | 0.064 | 0.450 |
| Sample 2 | 0.129 | 0.509 |
| Sample 3 | 0.103 | 0.492 |

Example 4

Firstly, 8 mol/L aqueous urea (2000 mL) was mixed with 0.2 mL dimercaptoethanol, thus obtaining a denaturing solution; then 140 mg crushed BSA inclusion body was mixed with 1400 mL of the denaturing solution obtained, thus obtaining a first inclusion body solution in a concentration of 0.1 mg/ml; to the first inclusion body solution obtained, 100 mL glycerinum was added as a cryoprotective agent, and used to adjust the ice point of the solution, thus obtaining a second inclusion body solution which was further adjusted to be of a pH value of 7.2 with a sodium carbonate solution; the container used for renaturing the BSA inclusion body was coated with several towels for keeping cool; the resulting mixture was subjected to a programmed cooling process at −25° C. overnight, then an ice block formed in the initial stage was subjected to thaw, thus obtaining a first mixture containing a renatured protein and its precursor; the first mixture was diluted by 5 times with the bovine serum albumin (BSA) ELISA kit (Shanghai Tong Wei Industrial Co., Ltd., TW p024497), thus obtaining a second mixture; finally, three random aliquots of each of the first mixture and the second mixture were detected respectively by the BSA ELISA kit for their activities, according to the manufacturer's instructions, with yellow color indicating the presence of activated proteins; and another three random aliquots of each of them were detected respectively by the WD-2102A automatic microplate reader (Beijing, Liu Yi) for their absorbance, with the detected results shown in Table 4 as follows.

TABLE 4

Absorbance of Each Sample

| No. | Absorbance | |
| --- | --- | --- |
| | Before dilution | After dilution by 5 times |
| Blank Control | 0.002 | 0.000 |
| Sample 1 | 0.021 | 0.846 |
| Sample 2 | 0.024 | 0.932 |
| Sample 3 | 0.187 | 1.036 |

Reference throughout this specification to "an embodiment", "some embodiments", "one embodiment", "another example", "an example", "a specific example" or "some examples" means that a particular feature, structure, material or characteristic described in connection with the embodiment or example is included in at least one embodiment or example of the present disclosure. Thus, the appearances of the phrases such as "in some embodiments", "in one embodiment", "in an embodiment", "in another example", "in an example", "in a specific example" or "in some examples" in various places throughout this specification are not necessarily referring to the same embodiment or example of the present disclosure. Furthermore, the particular features, structures, materials or characteristics may be combined in any suitable manner in one or more embodiments or examples. In addition, it will be apparent to those skilled in the art that different embodiments or examples as well as features of the different embodiments or examples described in this specification may be combined without contradictory.

Although explanatory embodiments have been shown and described, it would be appreciated by those skilled in the art that the above embodiments cannot be construed to limit the present disclosure, and changes, alternatives and modifications can be made in the embodiments without departing from spirit, principles and scope of the present disclosure.

What is claimed is:

1. A method of treating a protein to be renatured, comprising:
    (1) mixing the protein to be renatured with a denaturing solution containing a denaturing agent, a reducing agent and a cryoprotective agent to produce a resulting mixture;
    (2) incubating the resulting mixture at a reduced temperature such that the denaturing agent is gradually precipitated from the denaturing solution, resulting in a decreasing concentration gradient of the denaturing agent and an increasing concentration of a renatured protein or its precursor in the denaturing solution with a decreasing volume;
    (3) obtaining at least one of the renatured protein and its precursor; and,
    (4) subjecting the at least one of the renatured protein and its precursor obtained in the step (3) to a dilution method, such that the precursor is further renatured to become the renatured protein;
    wherein incubating the resulting mixture is conducted in a container provided with at least one snubber partition disposed along a horizontal or vertical direction.

2. The method according to claim 1, wherein the at least one of the renatured protein and its precursor is present in at least one form of a solution and a frozen body.

3. The method according to claim 1, wherein in the step (2), the resulting mixture is incubated under at least one of an electric field, a magnetic field, a high pressure and a sound wave.

4. The method according to claim 1, wherein the denaturing agent is a chemical agent adapted for opening a secondary bond effectively so as to keep a peptide chain in a free extended condition.

5. The method according to claim 4, wherein the denaturing agent is selected from at least one of urea and guanidine hydrochloride.

6. The method according to claim 5, wherein the denaturing agent is of an initial concentration greater than 4 mol/L.

7. The method according to claim 1, wherein the reducing agent is a material capable of destroying a disulfide bond so as to produce a reduced thiol.

8. The method according to claim 7, wherein the reducing agent is selected from one or more of dimercaptoethanol, dithiothreitol, tris-(2-carboxyethyl)phosphine, reduced glutathione, ascorbic acid, hydrogen sulfide and sodium thiosulfate.

9. The method according to claim 1, wherein the denaturing solution is of a pH value of 4.0 to 10.0.

10. The method according to claim 1, wherein the low temperature in the step (2) is below 4° C.

11. The method according to claim 1, wherein the protein to be renatured in the denaturing solution is of an initial concentration of 0.001 μg/ml to 30 mg/ml.

12. The method according to claim 1, wherein at least a part of the protein to be renatured is in a structural form of an inclusion body.

13. The method according to claim 1, wherein each of the at least one snubber partition is of a cross section consisting of a plurality of equilateral polygons.

14. The method according to claim 13, wherein the cross section is in a honeycomb shape consisting of a plurality of hexagons with a side length of 0.5 cm to 4.0 cm.

15. The method according to claim 13, wherein the at least one snubber partition includes at least two snubber partitions disposed along the horizontal or vertical direction and parallel to each other, with the equilateral polygons in different snubber partitions being a same shape but in same or different side lengths.

16. The method according to claim 1, wherein the protein to be renatured in the denaturing solution is of an initial concentration of 0.1 mg/ml.

* * * * *